United States Patent [19]

Sarrine

[11] 4,350,147
[45] Sep. 21, 1982

[54] ENDOSCOPE

[75] Inventor: Robert J. Sarrine, Ann Arbor, Mich.

[73] Assignee: Transidyne General Corporation, Ann Arbor, Mich.

[21] Appl. No.: 190,528

[22] Filed: Sep. 24, 1980

[51] Int. Cl.³ .............................................. A61B 1/00
[52] U.S. Cl. ....................................................... 128/4
[58] Field of Search .......... 128/770, 302, 305, 329 R, 128/361, 3–11

[56] References Cited

U.S. PATENT DOCUMENTS 3,685,509  8/1972  Bentall ............................... 128/305
4,219,013  8/1980  Okada ................................... 128/4

OTHER PUBLICATIONS

"A Comprehensive Guide to Purchasing", Mueller & Co., p. 22, Catalogue No. 65, Mar. 16, 1964.

*Primary Examiner*—Robert Peshock
*Attorney, Agent, or Firm*—Krass, Young & Schivley

[57] ABSTRACT

A multi-segmented endoscope (20) includes at least two sections (22), (24) which are detachably coupled together to provide endoscopes of varying lengths and openings for use during different stages of the birth process. The end (26) of the smaller section (22) is angled complementarily with respect to the fetus to insure a good seal to prevent contamination of blood samples taken from the infant.

12 Claims, 8 Drawing Figures

ENDOSCOPE

DESCRIPTION

1. Technical Field

This invention relates generally to medical instruments and more particularly to endoscopes used in conjunction with other medical apparatus during fetal blood sampling.

2. Background Art

Fetal blood sampling is extensively employed during birth if a physician suspects that the fetus may be receiving an improper amount of oxygen due, for example, to strangulation by the unbilical cord or premature separation of the placenta. Conventionally such sampling involves inserting an endoscope through the birth canal and pressing it against the fetal presentation. The presenting field is illuminated by a small light which is positioned in a fixed manner on the larger or proximal end of the endoscope. The presenting field or puncture area is cleaned of body fluids by using long swabs which are inserted through the endoscope and a silicone jelly is applied to induce a large drop of blood to form when the skin is punctured.

It should be noted that if the endoscope does not seal properly against the fetal presentation the puncture area will become contaminated by body fluids and the procedure must be started over. Once an uncontaminated field is prepared, the physician then introduces a lancet through the endoscope to make an incision. After the incision is made, the lancet is removed and a long glass capillary tube is advanced to collect the blood sample. The blood is then tested for its PH value which is a function of the amount of oxygen in the blood.

This conventional technique is illustrated in FIGS. 1 and 2. It is well known that there are several dynamically varying geometries during the birth process. The length of the birth canal, the dilation of the cervix, and the angle of the fetal presentation with respect to the birth canal all vary during the birth process. During early stages of birth, the tangent of the fetal presentation lies at a rather substantial angle with respect to the centerline of the birth canal as shown in FIGS. 1 and 2. Making a good seal against the infant's head with the endoscope at this stage of the birth process is extremely difficult. In FIG. 1 a conventional endoscope 10 is shown inserted through vagina 12 until the end of the endoscope is near cervix 14. In order to make a good seal between the oblique angle of the end of endoscope 10 and the infant's head 16, the doctor must stretch vagina 12 in an effort to locate the infant's head 16 through the cervix 14 as shown in FIG. 2. Due to the geometries involved, considerable pain is experienced by the mother during the stretching of the vaginal tissues and it is still difficult to get a good seal between the end of endoscope 10 and the baby's head 16. Accordingly, the possibility of contamination of the subsequently taken blood sample is greatly increased.

One attempt to deal with the problems noted above is disclosed in U.S. Pat. No. 3,685,509 to Bentall which discloses a blood sampling endoscope having an evacuated tubular end portion for adhering to the fetal presentation. The endoscope includes a custom formed capillary tube, a freely moveable lancet, and a vacuum tube as part of the device. The use of this device has several drawbacks. It introduces a new requirement for additional equipment since suction must be applied to the annulus of the endoscope. The necessity for additional equipment may be both costly and burdensome. The additional wall thickness of the endoscope which contains the evacuated tube may require that the cervix be dialated more than is required with a thinner walled conventional endoscope. The external capillary and suction tubes may add to the difficulty of insertion and interfere with the movement of the endoscope when in position, e.g. when adjustments are made to accommodate movement of the mother or fetus. The fact that the capillary tube is captured in this endoscope limits the movement of the capillary tube thereby making interception with the blood more difficult. The additional length of the endoscope that accommodates the lancet handle and the bent end of the capillary tube requires that the procedure be carried out at a more distant point of vision than would normally be required, especially during the latter stages of the birth process when the fetal presentation is relatively close. As with conventional endoscopes, the distal end of the Bentall device is also terminated at a 90° angle with respect to its longitudinal axis.

The present invention is directed to solving one or more of the problems set forth above.

DISCLOSURE OF THE INVENTION

According to one aspect of the invention the distal end of a hollow cylinder is terminated at an angle which complements the tangent of the fetal presentation with respect to the centerline of the birth canal. Thus, a better sealing arrangement is provided for use in fetal blood sampling during relatively early stages of the birth process. Another aspect of this invention revolves around the use of a multi-segmented endoscope, with each section being detachably connected to adjacent sections so as to provide endoscopic devices of various lengths for use in engaging the presenting part during different stages of the birth process. Preferably, the end of the smallest section terminates at the complementary angle described above. Larger sections have distal ends which are generally terminated at about 90° to the longitudinal axis and are designed for use during later stages of the birth process when a short, larger diameter endoscope is needed when the infant is lying substantially parallel to the birth canal and the cervix is quite dilated. The smaller section will function as an extender to the larger section and will be used during earlier stages of the birth process when the cervix is small and the birth canal is relatively long.

BRIEF DESCRIPTION OF THE DRAWINGS

These and other objects and advantages of the present invention will become apparent upon reading the following specification and by reference to the drawings in which.

BEST MODE FOR CARRYING OUT THE INVENTION

Figure 1:
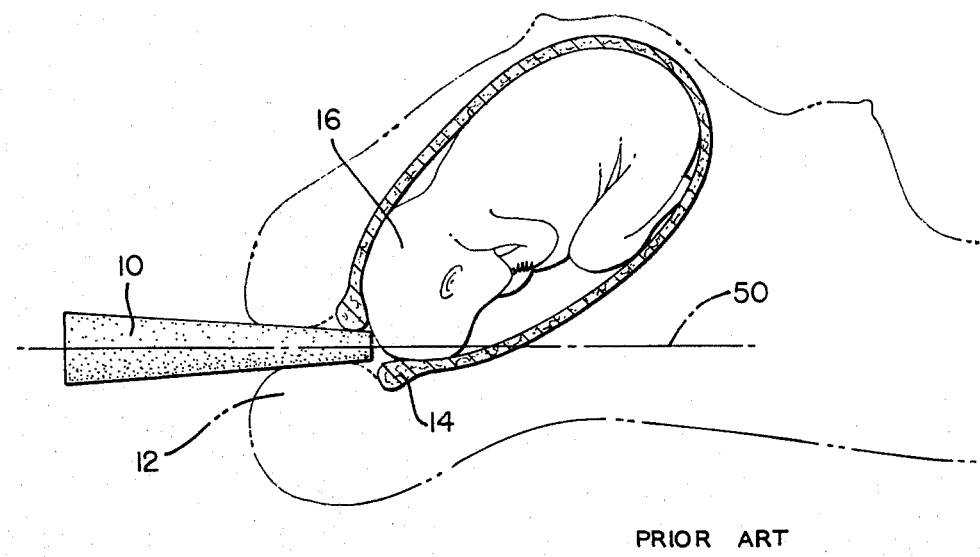
FIGS. 1–2 illustrate the use of conventional endoscopes shown in the prior art.
Figure 2:
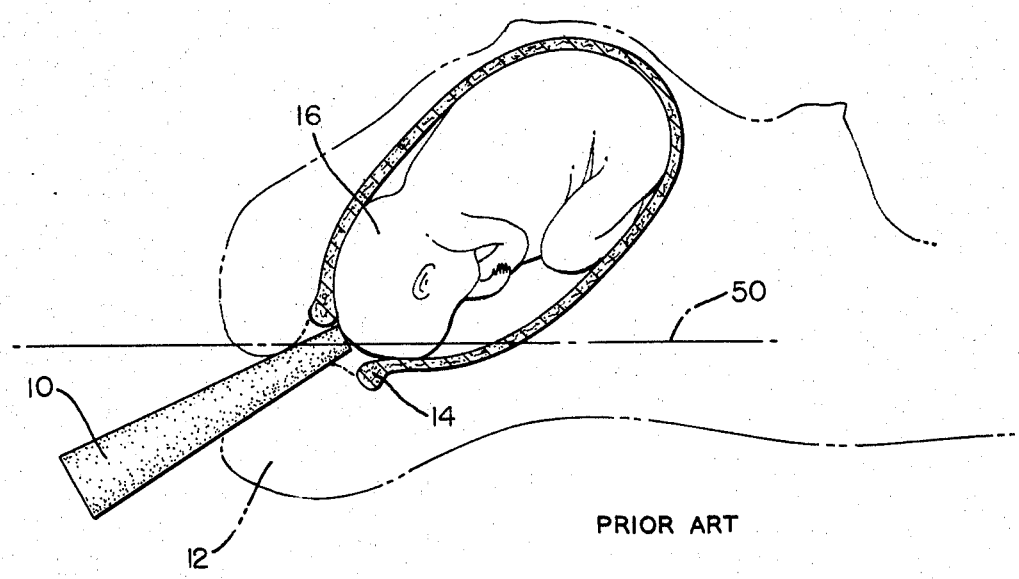
Figure 3:
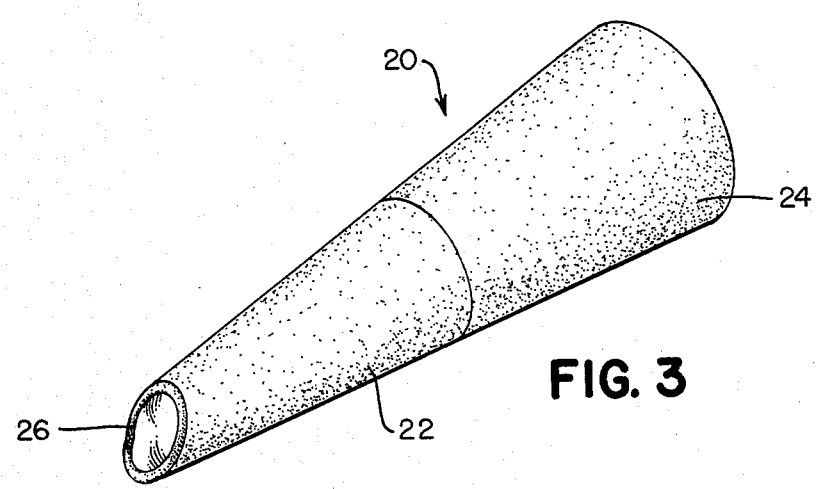
FIG. 3 is a perspective view of the preferred embodiment of the present invention.
Figure 4:
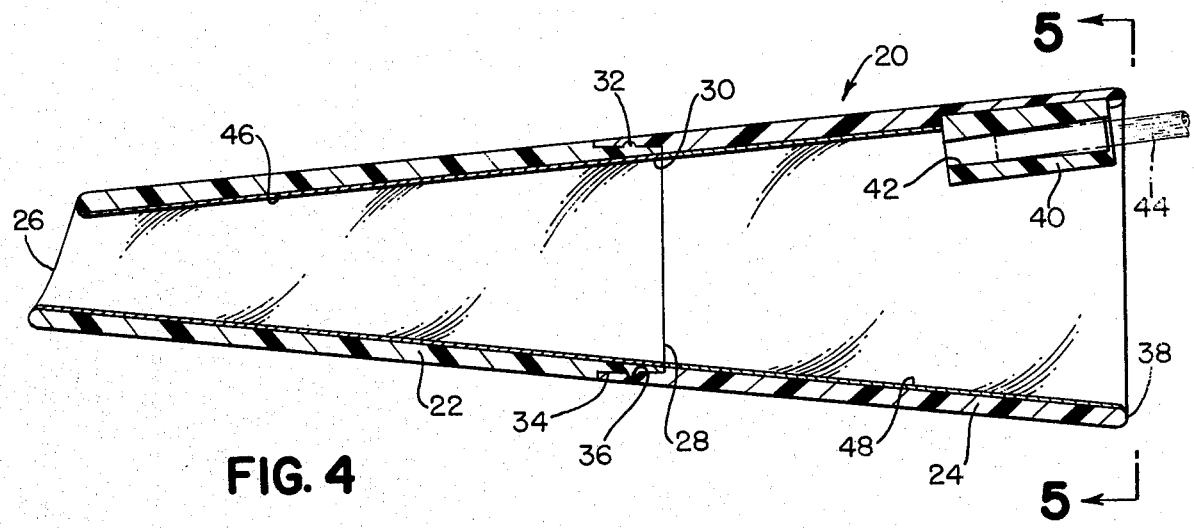
FIG. 4 is a cross-sectional view thereof.
Figure 5:
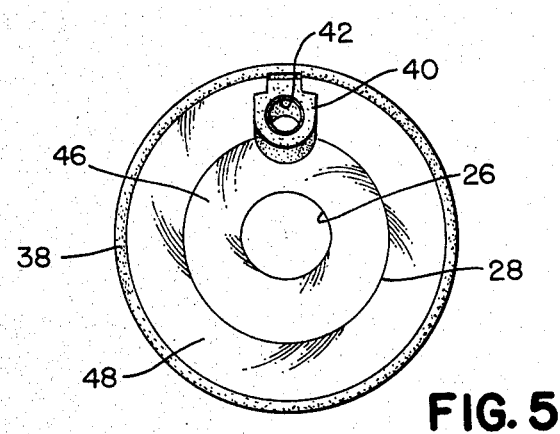
FIG. 5 is an end view thereof along lines 5—5 of FIG. 4.

With special reference to FIGS. 3-5, the preferred embodiment of this invention is characterized by an endoscope 20 having multiple sections detachably coupled together. Smaller section 22 and larger section 24 cooperate to form a continuous hollow conical cylinder which in this embodiment is about 8.4 inches in length. Preferably, each section is made of medically approved plastic such as virgin polypropylene.

The distal end 26 of the smaller section 22 is adapted to engage the fetus during relatively early stages of the birth process when the infant lies at an angle with respect to the birth canal. End 26 is angled with respect to the transverse axis of endoscope 20. The angle is chosen to be substantially complementary to the angle made by the tangent of the fetal presentation with respect to the centerline of the birth canal. The angle of end 26 is within the range of 5-30 degrees, the preferred embodiment being at an angle of about 15°. End 26 is also curved inwardly in this embodiment to conform as much as possible to the rounded fetal presentation. The curvature has a radius of about 2-2½ inches taken from a point obliquely spaced from the tangent of end 26 passing through the centerline thereof.

The opening at distal end 26 of the smaller section 22 is about 0.85 inch in diameter. The walls of the smaller section diverge from end 26 to provide an opening of about 1.425 inch at the proximal end 28. End 28 includes a generally concentric flange 30 indented from the normal projections of the outer surfaces of section 22. Flange 30 includes a radially outwardly projecting snap ring 32 which may be integrally formed.

The distal end 34 of larger section 24 is terminated at about 90° with respect to the longitudinal axis of endoscope 20. A groove 36 on the inner wall of section 24 near the distal end 34 provides a mating surface into which snap ring 32 may nest. Preferably, the walls of larger section 34 are thinner in the area for receiving the telescoping flange portion 30 of the smaller section 22 such that the inner surfaces of the two sections are substantially continuous.

While other connecting constructions may be envisioned, the present design has several advantages. The structure is relatively simple and may be formed integrally with the cylinders making up each section. A substantially rigid structure is provided when the two sections are attached together. However, only about 2 kilograms of force is needed to separate the two sections. When the sections are separated, the end 34 of larger section 24 is used to engage the fetal presentation. The design of the coupling is such that the end 34 remains free of irregularities which could effect its sealing of properties. End 34 defines an opening about 1.425 inch, with the walls of section 24 diverging toward proximal end 38 defining an opening of about 2 inches in diameter.

Provision may be made for accommodating a light emitting device to aid in viewing the operation. In this embodiment, a member 40 is attached to the wall of larger section 24 near the proximal end 38. A tapered bore 42 in member 40 is adapted to receive a fiber optic light 44. In this example, bore 42 converges from an opening of about 0.275 inch to 0.25 inch such that the fiber optics light 44 may be press fit into bore 42.

According to a feature of this invention, the inner wall surfaces 46 and 48 of smaller section 22 and larger section 24, respectively, are coated with a reflective material to provide mirror finishes. This may be accomplished by a wide variety of methods such as vacuum deposition. Thus, in the event that the physician cannot position himself to see completely through endoscope 20, he can observe the blood collecting process by looking at the reflection off of wall surfaces 46 and/or 48.

INDUSTRIAL APPLICABILITY

Figure 6:
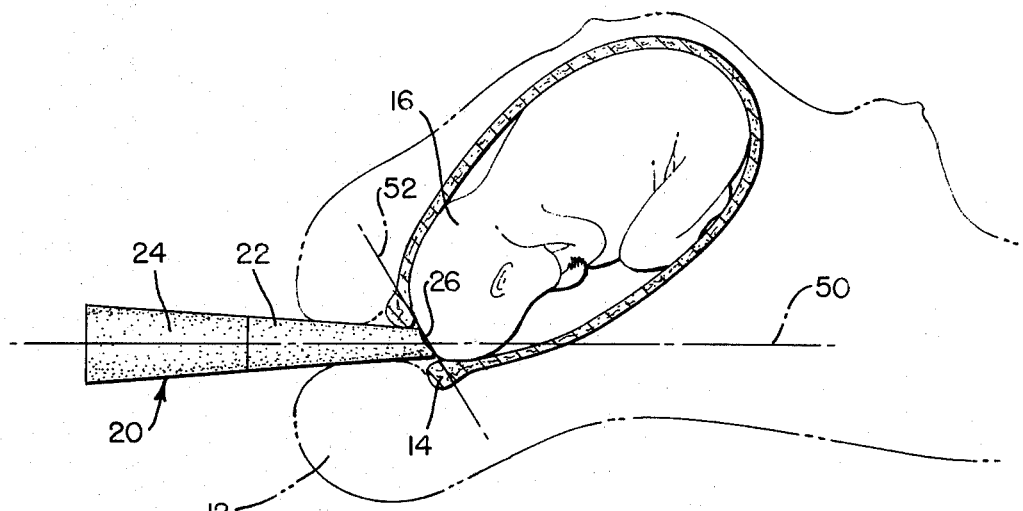
FIGS. 6–8 illustrate a method of using the device of the present invention.
Figure 7:
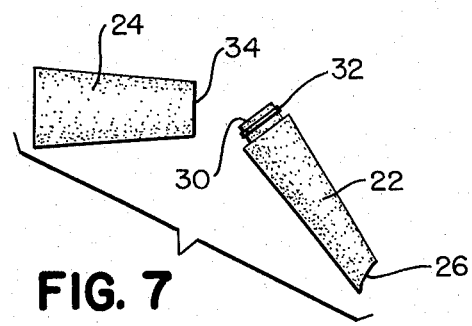
Figure 8:
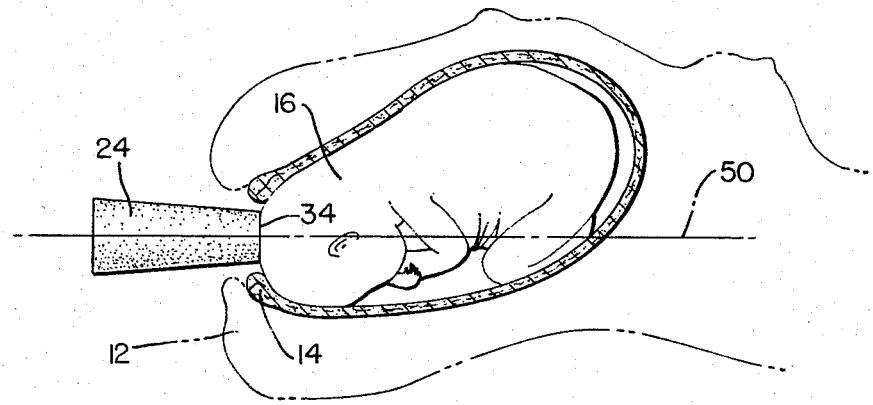

FIGS. 6-8 illustrate the advantages of using the endoscope 20 of the preferred embodiment. FIG. 6 shows the use of endoscope 20 during relatively early stages of the birth process in which the infant lies at an angle with respect to the centerline 50 of the birth canal made up of vagina 12 and cervix 14. The tangent 52 of the infant's head 16 is at a generally obtuse angle with respect to birth canal centerline 50. Note also that the birth canal has considerable length. At this stage of the birth, sections 22 and 24 of endoscope 20 are connected together such that smaller end 22 acts as an extender to accommodate for the relatively long length of the birth canal. The smaller diameter opening of end 26 makes it easier to engage head 16 through the cervix 14 which has been dilated only to a limited extent. Moreover, the angled orientation and curved shape of end 26 facilitates a good seal with the infant's head 16. The stretching of the vaginal tissues 12 associated with the prior art is substantially eliminated thereby minimizing discomfort.

FIG. 8 shows the birth process at a later stage of development. Note that the cervix 14 is much more dilated and that the birth canal is considerably shorter in length. The fetus has also rotated into a position which is almost parallel with the birth canal. Under these conditions, endoscope 20 is broken apart as shown in FIG. 7 to separate the smaller section 22 from the larger section 24. The end 34 of section 24 has a larger diameter opening to accommodate the dilated cervix and an oblique angle to complement the angle at which the infant now lies. The shorter length of section 24 permits the physician to operate at a much closer distance to the infant. Accordingly, blood samples may be taken much easier and without the fear of contamination.

It can now be realized that the present invention provides a multipurpose endoscope which greatly facilitates the blood collecting process from an infant during birth. While the preferred embodiment is shown having only two sections, the teachings of the present invention are broad enough to encompass more sections in order to provide a segmented endoscope providing different lengths and end openings for use during different stages of the birth process. Other modifications will become apparent to one skilled in the art upon a study of the specification, drawings, and claims.

I claim:

1. An endoscope (20) comprising a hollow, conical cylinder divided into multiple sections (22), (24), each section being detachably connected (30), (32)-(36) to adjacent sections whereby to provide endoscopes of various lengths and of different size openings (26), (34) for use in engaging a presenting part (16) at different stages in the birth process, the distal end (26) of a section (22) being sloped at an angle with respect to the transverse axis of the cylinder.

2. The endoscope of claim 1 wherein said angle is between 5-30 degrees.

3. The endoscope of claim 1 wherein said distal end (26) of the smaller section (22) is curved inwardly to substantially conform to a rounded shape of the presenting part (16).

4. The endoscope of claim 1 wherein the proximal end (28) of a smaller section (22) and the distal end (34) of the next adjacent larger section (24) are connected together at about 90° with respect to the longitudinal axis of the cylinder whereby said larger section (24) provides an endoscope of shorter length with a larger opening at a complementary angle to the presenting part (16) for use in later stages of the birth process.

5. The endoscope of claim 4 wherein said smaller section (22) includes means (30), (32), (36) on its proximal end (28) for engaging inner walls (48) near the distal end (34) of the adjacent larger section (24) whereby the distal end (34) of the larger section (24) remains free of surface irregularities.

6. The endoscope of claim 5 wherein said larger section (24) includes a groove (36) in its inner wall inboard of its distal end (34), and wherein said proximal end (28) of the smaller section (22) includes an annular flange (30) with a snap ring (32) for engaging the groove.

7. The endoscope of claim 1 wherein inner wall surfaces of the sections include mirror finishes (46), (48).

8. The endoscope of claim 1 which includes a member (40) having a tapered bore (42) into which a light (44) may be press fit for viewing the presenting part (16).

9. An endoscope (20) comprising a hollow cylinder (22) having a sloped end portion (26) angled at about 5–30 degrees with respect to the transverse axis of the cylinder to thereby complement the angle between the tangent (52) of the presenting part (16) with respect to the centerline (50) of the birth canal.

10. The endoscope of claim 9 wherein said end portion (26) is curved inwardly to substantially conform with rounded surfaces of the presenting part (16).

11. The endoscope of claim 10 wherein said cylinder (22) is detachably connected to another cylinder (24).

12. An endoscope comprising a hollow, conical cylinder (22) having a sloped end portion (26) angled at about 15 degrees with respect to the transverse axis of the cylinder to thereby provide a surface for engaging a presenting part in a birth canal at an angle substantially complementary to the angle between the tangent (52) of the presenting part (16) with respect to the centerline (50) of the birth canal.

* * * * *